United States Patent
Koczab

[11] Patent Number: 5,843,064
[45] Date of Patent: Dec. 1, 1998

[54] NON WOVEN MATERIAL AND HYGIENIC ABSORBENT ARTICLE COMPRISING SUCH MATERIAL

[75] Inventor: Jean Pierre Koczab, Bondues, France

[73] Assignee: Peaudouce, Linselles, France

[21] Appl. No.: 826,400

[22] Filed: Mar. 24, 1997

Related U.S. Application Data

[63] Continuation of Ser. No. 436,286, May 17, 1995, abandoned.

[30] Foreign Application Priority Data

Nov. 20, 1992 [FR] France .................................. 92 13997

[51] Int. Cl.⁶ ...................................................... A61F 13/16
[52] U.S. Cl. ................................................................ 604/378
[58] Field of Search ...................................... 604/378, 358, 604/385.1, 383, 374; 428/98, 101, 172, 212, 221

[56] References Cited

U.S. PATENT DOCUMENTS

| | | | |
|---|---|---|---|
| 3,206,351 | 9/1965 | Smith | 604/378 |
| 3,967,623 | 7/1976 | Butterworth et al. | 604/383 |
| 4,223,677 | 9/1980 | Anderson . | |
| 4,324,247 | 4/1982 | Aziz | 604/385.1 |
| 4,806,411 | 2/1989 | Mattingly, III et al. | 604/385.1 |
| 4,826,498 | 5/1989 | Koczab | 604/378 |
| 4,883,707 | 11/1989 | Newkirk | 604/378 |
| 4,985,279 | 1/1991 | Mussallem, III . | |
| 5,135,521 | 8/1992 | Luceri et al. | 604/383 |

FOREIGN PATENT DOCUMENTS

| | | |
|---|---|---|
| 1182604 | 2/1985 | Canada . |
| 0151018A3 | 8/1985 | European Pat. Off. . |
| 0232729A1 | 8/1987 | European Pat. Off. . |
| 0252041A3 | 1/1988 | European Pat. Off. . |
| 0306262A1 | 3/1989 | European Pat. Off. . |
| 0313800A1 | 5/1989 | European Pat. Off. . |
| 0352208A1 | 1/1990 | European Pat. Off. . |
| 2169348 | 7/1973 | France . |
| 3029315 | 2/1981 | Germany . |
| WO 91/11164 | 8/1991 | WIPO . |

*Primary Examiner*—John G. Weiss
*Assistant Examiner*—David J. Cho
*Attorney, Agent, or Firm*—Burns, Doane, Swecker & Mathis LLP

[57] ABSTRACT

Multilayer nonwoven material which has a high rate of drying out, improved rate of entry of, or break-through time by, body fluids and good diffusion of the body fluids in the plane of the layers. The multilayer nonwoven material comprises at least two superposed layers (1, 2) of natural or synthetic textile fibers, joined together, the fibers of the successive layers having a denier decreasing progressively, in a given direction, from one successive layer to the other.

Application as surface webs for absorbent articles of hygiene.

12 Claims, 4 Drawing Sheets

NON WOVEN MATERIAL AND HYGIENIC ABSORBENT ARTICLE COMPRISING SUCH MATERIAL

This application is a continuation of application Ser. No. 08/436,286, filed May 17, 1995, now abandoned.

BACKGROUND OF THE INVENTION

1. Field of the Invention

The invention relates generally to a composite nonwoven material made up of a number of layers or sheets of textile fibers.

More particularly, the invention relates to a composite nonwoven material made up of a number of layers in which the fibers have a denier (measure of the diameter or of the thickness of the fibers) which decreases in a given direction, from one successive layer to the other.

The invention also relates to an absorbent article of hygiene such as a diaper or dressing for an incontinent person comprising surface web or sheet (also referred to as covering web or sheet) a web consisting of multilayer nonwoven material in which the layer made with the fibers of lower denier is situated directly on the absorbent pad of the article.

The invention also relates to an absorbent article of hygiene such as a diaper or dressing comprising, in addition to the surface web, a crotch region strip consisting of the multilayer nonwoven material, arranged on the surface web or between the surface web and the absorbent pad of the article, in which the layer of fibers made of the fibers of lower denier is situated directly in contact with the surface web or the absorbent pad respectively.

2. Discussion of Related Art

Absorbent articles of hygiene such as diapers and dressings for an incontinent person generally comprise a pad or mat of absorbent material on which a surface web or sheet is arranged. When the articles are in use, this surface web or sheet is in direct contact with the skin and its purpose is to isolate the skin from the moist absorbent pad. This web must therefore have certain properties, namely a pleasant contact with the skin, allow a rapid passage of the body fluid through as far as the absorbent pad, ensure good diffusion of the liquids over the whole surface of the absorbent pad, and avoid a rise of the body fluids absorbed by the pad towards the upper surface of the web.

Absorbent pads or mats have recently been developed which contain particles of superabsorbent material, generally arranged between two layers of fibers, themselves included between a base layer generally made of nonwoven material and an upper layer in contact with the skin, generally made of cotton wadding or of a nonwoven material. Such a type of pad is described in EP-A-0,232,729. In order to obtain a maximum efficiency of the superabsorbent materials contained in these pads it is desirable that the liquid should diffuse or be distributed over the whole upper surface of the absorbent mat. The surface webs or sheets arranged on the upper surface of such pads generally consist of one or more layers of a nonwoven material.

Document FR-A-2,588,285 describes a multilayer nonwoven textile which has at least two layers of nonwoven web, one of the layers being made up of fibers of bilobed cross-section and the other layer being made up of fibers of trilobed cross-section. Each web layer is preferably obtained by the spinning bonding technique (spun nonwoven) and the two web layers are joined to form the multilayer nonwoven by heat bonding in noncontinuous compacted regions.

Document WO 87/07,117 describes an absorbent article of hygiene comprising an absorbent body surrounded by a cover. This cover or surface web consists of two layers of nonwoven material. The first layer of nonwoven material, in contact with the user's skin, consists of a thin layer of fibrous spin-bonded tissue (spun nonwoven) made of a hydrophobic material, and the second layer in contact with the absorbent body is a hydrophobic fibrous layer of tissue of melt-bonded fibers, similar in construction to the first layer. These two layers of surface web are not bonded together in the region intended to come into contact with the user's body.

Document WO 88/05,269 relates to a surface web for a disposable absorbent article made up of at least two layers of nonwoven which may be identical or different and which are joined by lines of adhesive forming an open pattern.

OBJECTS AND SUMMARY

Although such surface webs or sheets have an appropriate rate of entry, or break-through by, body fluids and ensure a certain diffusion of the liquid on the surface of the absorbent mat or pad, it is always desirable to improve these characteristics. Moreover, it is also desirable to obtain a maximum reduction of any return of the body fluids, in order to obtain a surface web which dries out rapidly and which does not rewet.

An aim of the present invention is therefore to provide a nonwoven material which has an improved rate of entry of, or time for break-through by, the body fluids, which dries out rapidly, which ensures good diffusion of the body fluids over the whole surface of the absorbent mat, and which reduces as much as possible any rise of the body fluids absorbed by the mat.

Another aim of the invention is to provide an absorbent article of hygiene such as a diaper or dressing for an incontinent person, comprising an absorbent pad or mat provided at its surface with a surface web or sheet made of the multilayer nonwoven material of the present invention.

Another aim of the present invention is to provide an absorbent article of hygiene such as a diaper or dressing for an incontinent person, comprising an absorbent pad or mat, a surface web made of traditional nonwoven material, and, to complement the traditional surface web, a strip of similar width to that of the crotch region of the absorbent pad and of length similar to that of the pad, consisting of a multilayer nonwoven material according to the invention.

According to the present invention, a multilayer nonwoven material is produced which comprises at least two superposed layers of natural or synthetic textile fibers, joined together, in which the fibers of the successive layers have a denier decreasing progressively, in a given direction, from one successive layer to the other.

The invention also provides an absorbent article of hygiene which comprises an outer layer made of material which is impervious to body fluids, an absorbent pad which is permeable to body fluids and bonded to the outer layer, and a surface web permeable to the body fluids and bonded to the outer layer, in which the surface web consists of a multilayer nonwoven material comprising at least two superposed layers of natural or synthetic textile fibers joined together, the fibers of the successive layers having a denier decreasing progressively from one successive layer to the other, the layer having the fibers of lower denier being situated directly on the internal surface of the absorbent pad.

According to another embodiment of the invention, an absorbent article of hygiene is provided which comprises an outer layer made of material which is impervious to body fluids, an absorbent pad which is permeable to body fluids and bonded to the outer layer, a surface web made of material permeable to body fluids and bonded to the outer layer, and in addition to this surface web an additional crotch region strip with a width similar to that of the crotch region of the absorbent pad and a length similar to that of the pad and consisting of at least two superposed layers of natural or synthetic textile fibers joined together, the fibers of the successive layers having a denier decreasing progressively from one successive layer to the other, the layer of fibers of lower denier forming, in the article of hygiene, the outermost layer of the strip, that is to say the layer closest to the absorbent pad, and the layer of fibers of higher denier forming the innermost layer of the strip, that is the layer furthest away from the absorbent pad.

An important characteristic of this nonwoven material lies in the fact that the various superposed layers consist of fibers whose denier (unit measuring the thickness or the diameter of the fibers) varies from one layer to the next with a progressive decrease from an inner or surface layer to an outer or base layer. A fibrous structure is thus obtained in which the diameter of the pores decreases from the inner to the outer layer. Any suitable natural or synthetic fibers, for example cellulose, viscose, polyester, polyethylene, polypropylene or ethylene-propylene copolymer fibers may be employed for the manufacture of the nonwoven layers. The various layers may be made up of fibers of the same kind or of different kinds. These layers or sheets of textile fibers may be formed by any process employed for the manufacture of nonwoven material, such as by spin-bonding, spin-lacing, chemical bonding, heat bonding, needling, air-laying or tangling by jets of water. As indicated, the multilayer nonwoven material comprises at least two layers of fibers of different denier, but may comprise a larger number of layers, for example three or more. In one embodiment, which is recommended, the nonwoven material according to the invention is made up of two layers of fibers with denier decreasing from the inner to the outer layer. In this embodiment the layer of fibers of higher denier generally has a denier of between 3.3 and 6.6, while the layer of lower denier generally has a denier of between 1.5 and 3.3. In another embodiment of the invention the nonwoven material is made up of five layers of fibers such that all of the fibers in each layer have a denier decreasing from the inner layer to the outer layer. In this embodiment comprising five layers, the denier of the fibers is preferably chosen, in the case of each of the successive layers, from the layer of fibers of higher denier to the layer of fibers of lower denier, in the following ranges:

layer 1 (the innermost layer): 6.6 to 9 layer 2: 4.4 to 6.5 layer 3: 3.3 to 4.3 layer 4: 1.7 to 3.2 layer 5 (the outermost layer): 0.8 to 1.6.

In general, the layers of the multilayer nonwoven according to the invention have a weight per unit area of between 5 and 50 g/m$^2$, preferably between 5 and 30 g/m$^2$. In addition, in a recommended embodiment some of the layers may be treated with appropriate surface or oiling agents which are well known in the art for imparting hydrophilicity characteristics thereto. These treated layers have the advantage of increasing the rate break-through by body fluids, while the untreated layers have properties of diffusion of the fluids in their plane, and this ensures better distribution or diffusion of the body fluids over the whole surface of the absorbent mat. The layers of hydrophilic and hydrophobic nature may be advantageously alternated. The hydrophilic or hydrophobic nature of the various layers can be obtained by employing different conventional processes of manufacture for each of the layers.

The various layers of the multilayer nonwoven material are joined together by any appropriate technique, for example heat-bonding or mechanical bonding, in particular by needling or by tangling by jets of water. A recommended method of joining the layers according to the invention is needling.

Such a material is particularly useful for the manufacture of surface webs or sheets or of crotch region strips employed as a replacement for or addition to the conventional surface web in absorbent articles of hygiene such as diapers and dressings for an incontinent person.

When it is employed as a surface web of an absorbent article of hygiene, replacing the conventional surface web, the multilayer nonwoven material of the present invention is arranged directly on the absorbent mat of the article with the layer consisting of fibers of lower denier in contact with the inner surface of the pad. Consequently, the layer of fibers of higher denier is found to be the upper or inner layer of the web which would be in contact with the user's skin. As a result, the layers which have a larger pore diameter are situated in the upper or inner part of the web and the layers which have a smaller pore diameter in the lower or outer part of the web. In this way a fast break-through of the upper layers of the web is obtained, and this ensures rapid drying out of these upper layers and an enhanced comfort of the user, while the presence of pores of smaller diameters in the lower layers of the web, and in particular directly above the pad reduces as much as possible any rise of the body fluids which have been absorbed by the absorbent pad.

When employed in addition to the conventional surface web of an absorbent article of hygiene, the multilayer nonwoven material according to the invention preferably forms a strip with a width similar to that of the absorbent pad in the crotch region. The length of the strip may correspond to that of the article of hygiene, but will be preferably equal to that of the absorbent pad. The strip made of multilayer nonwoven material according to the invention may be arranged, in the crotch region, either on the web made of conventional nonwoven material or between the web made of conventional nonwoven material and the absorbent pad. In both cases the innermost layer of the strip, that is to say the layer furthest away from the absorbent pad, is the layer of fibers of higher denier and consequently the outermost layer of the strip, that is to say the layer closest to the absorbent pad is the layer of fibers of lower denier. When this additional strip is situated above the conventional surface web it can be joined to the inner surface of the surface web by any conventional process such as, for example, adhesive bonding, heat-sealing, ultrasonic welding or needling. When this additional strip made of multilayer nonwoven material according to the invention is situated between the surface web and the absorbent pad, it can be bonded either to the outer surface of the surface web or to the inner surface of the absorbent pad by any conventional process, for example, adhesive bonding, heat-sealing, ultrasonic welding or needling

BRIEF DESCRIPTION OF THE DRAWINGS

The description which follows refers to the attached figures which show, respectively.

DETAILED DESCRIPTION OF THE PREFERRED EMBODIMENTS

Figure 1:
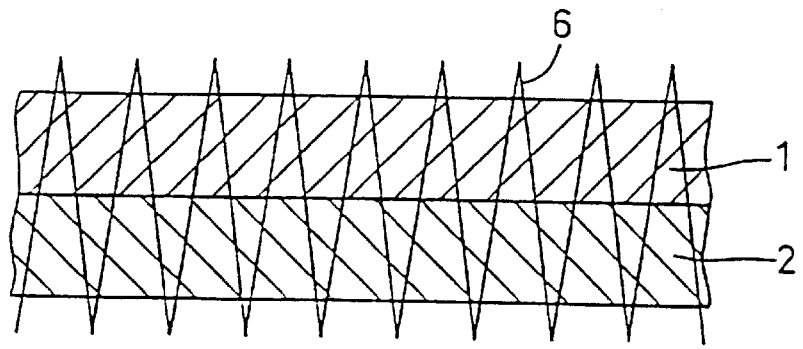
FIG. 1, a recommended embodiment of the multilayer composite nonwoven material according to the invention.

With reference to FIG. 1, a first embodiment of a multilayer composite material according to the invention is shown, which comprises two superposed layers of polyester fibers (1, 2) whose characteristics are the following, starting with the upper or inner layer 1 to the lower or outer layer 2. The inner layer consists of polyester fibers with a denier of between 3.3 and 6.6, preferably 6.6, and a weight per unit area of between 5 and 50 g/m$^2$, for example 41 g/m$^2$. The outer layer 2 consists of polyester fibers with a denier of between 1.5 and 3.3, preferably 3.3 or 1.5 deniers, and has a weight per unit area of between 5 and 50 g/m$^2$, for example 22 g/m$^2$. The layers are joined by needling or tangling by jets of water. The layers are preferably joined by a needling 6.

Figure 2:
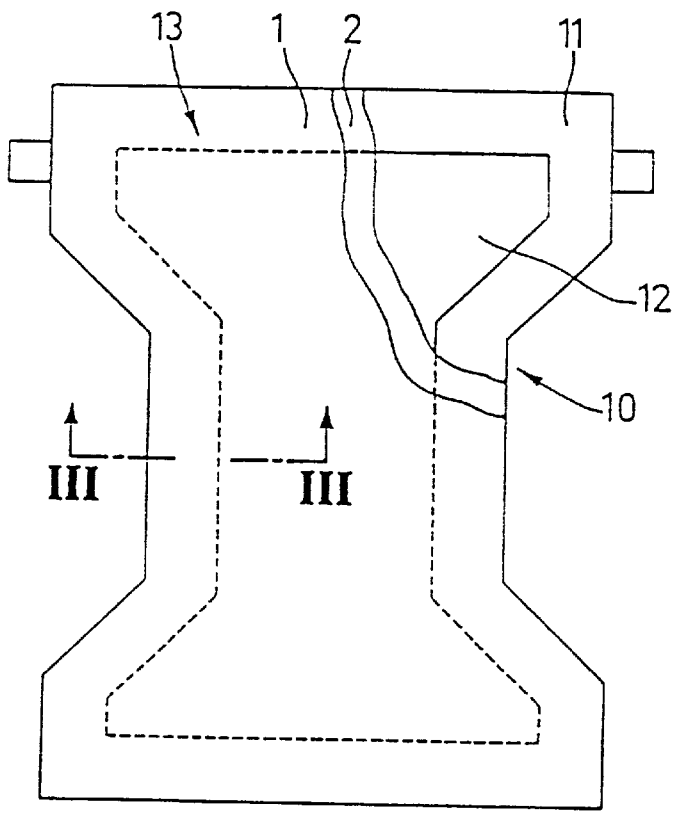
FIG. 2, a top view, with partial cutaway, of an absorbent article of hygiene such as a diaper, comprising a surface web made of material according to FIG. 1.
Figure 3:
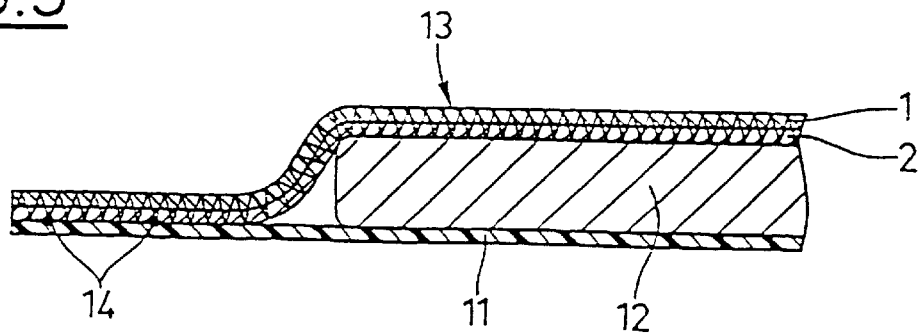
FIG. 3, a view in section along the line III—III of FIG. 2.

With reference to FIGS. 2 and 3, an absorbent article of hygiene 10, such as a diaper, is shown, comprising a surface web 13 made of multilayer composite nonwoven material according to the invention. The article of hygiene 10 comprises an outer layer 11 made of flexible material which is impervious to body fluids, on which there is arranged an absorbent mat or pad 12 which is permeable to body fluids, smaller in size than the outer layer 11 and bonded to the outer layer 11 by any appropriate means, for example by adhesive bonding. On this absorbent pad 12 there is a surface web 13 which is permeable to body fluids and of a size larger than that of the absorbent mat 12 and which is bonded to the outer layer 11 by any appropriate means such as adhesive bondings 14. As is well known, the outer layer 11, the absorbent pad 12 and the surface web 13 are generally in the form of an hourglass comprising two wide opposite end parts connected via a central crotch region part of general rectangular shape and of smaller width. As can be seen better in FIG. 3, in this embodiment the surface web 13 consists of the composite nonwoven material with two layers of FIG. 1. The lower or outer layer 2, consisting of fibers of lower denier is arranged directly on the pad 12, whereas the upper or inner layer made of fibers of higher denier forms the layer which will be in contact with the user's skin. This surface web 13 may be joined to the absorbent pad 12 by any conventional means such as adhesive bonding, heat-sealing, ultrasonic welding or needling.

In this way a diaper is obtained which has improved characteristics of rate of break-through and resistance to rewetting by the body fluids.

Figure 4:
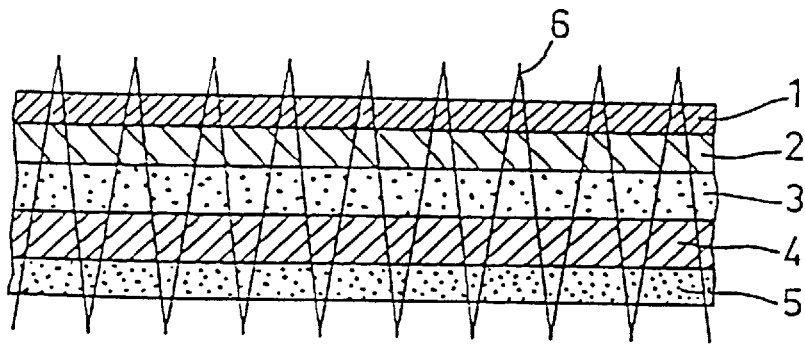
FIG. 4, another embodiment of a multilayer composite nonwoven material according to the invention.

With reference to FIG. 4, this shows an embodiment of a multilayer nonwoven material according to the present invention which is particularly appropriate for the replacement of the conventional surface web and which comprises five superposed layers of polyester fibers (1 to 5) whose characteristics are the following, starting from the upper or inner layer to the bottom or outer layer:

layer 1 6.6 deniers 30 g/m$^2$
layer 2 4.4 deniers 20 g/m$^2$
layer 3 3.3 deniers 20 g/m$^2$
layer 4 1.7 denier 15 g/m$^2$
layer 5 0.8 denier 15 g/m$^2$ The layers are joined by a needling 6 to obtain a final nonwoven web with a weight per unit area of 100 g/m$^2$. The needling density was 20 strokes/cm$^2$ and per face. Obviously, as already indicated, one or more of the layers may consist of fibers of another type such as, for example, viscose fibers or any other natural or synthetic textile fibers. In particular, the use of viscose fibers in some of the layers contributes retention to the sheet. In addition, the thickness of each individual layer and also that of the final product can be adjusted by adjusting the needling density, when a needling process is employed for forming each of the layers and/or for joining the layers together. Such a multilayer nonwoven material employed as surface web or as crotch region strip in addition to the surface web in an absorbent article of hygiene is characterized by fast drying-out of the material and improved rate of entry or break-through time by the body fluids, and a good diffusion of these fluids over the whole surface of the absorbent mat.

Figure 5:
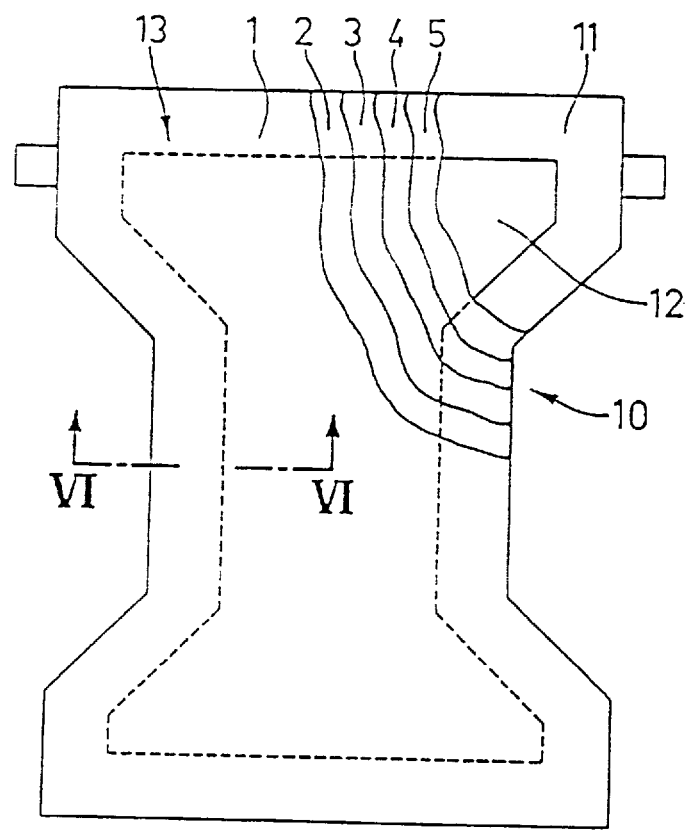
FIG. 5 a top view, with partial cutaway, of an absorbent article of hygiene, such as a diaper, comprising a surface web made of material according to FIG. 4.
Figure 6:
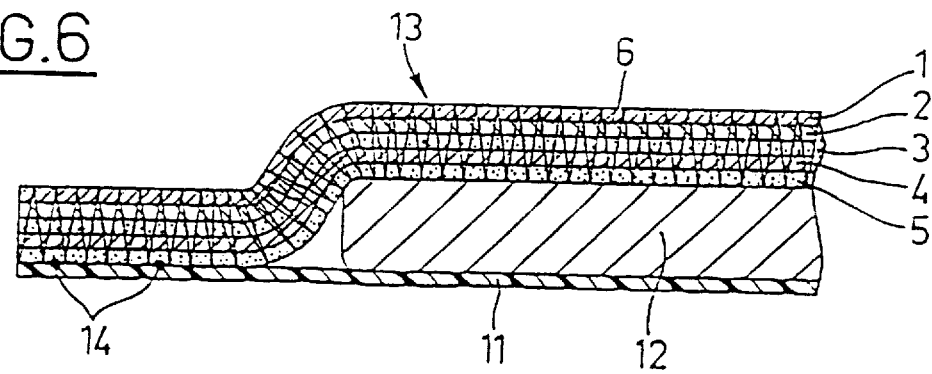
FIG. 6, a view in section along the line VI—VI of FIG. 5.

With reference to FIGS. 5 and 6, an absorbent article of hygiene 10, such as a diaper, has been shown, comprising a surface web 13 made of multilayer nonwoven material according to the invention. The article of hygiene 10 comprises an outer layer 11 made of a flexible material which is impermeable to body fluids, on which there is arranged an absorbent mat or pad 12 permeable to body fluids and smaller in size than the outer layer 11 and bonded to the outer layer 11 by any suitable means. On this absorbent pad 12 there is surface web 13 permeable to body fluids and of a size larger than that of the absorbent mat 12. As is well known, the outer layer 11, the absorbent pad 12 and the surface web 13 generally have the shape of an hourglass comprising two wide opposite end parts connected by a central crotch region part of general rectangular shape and smaller width. As can be seen better in FIG. 6, in a recommended embodiment, the surface web consists of five layers 1 to 5 of nonwoven material, such as, for example, the material of FIG. 4. The denier of the fibers of which each of the layers of nonwoven consists decreases progressively from the upper or internal layer 1 to the base or outer layer 5 which is directly in contact with the upper or internal surface of the absorbent pad. All the layers 1 to 5 are joined by needling 6. The surface web 13 made of multilayer nonwoven is bonded over its periphery to the impervious outer layer 11 by any suitable means, for example by adhesive bonding 14.

The layer 5 of the surface web 13 consisting of fibers of lower denier is thus situated directly on the absorbent pad 12, while the layer 1 consisting of fibers of higher denier is found to be the upper or internal layer of the web which will be in contact with the user's skin. The surface web 13 therefore has a pore diameter which decreases progressively from the upper or inner layer 1 to the base or outer layer 5, and this results in a rapid drying out of the surface of the web 13 and an increased barrier effect in respect of the rewetting by the fluids absorbed by the pad 12.

Figure 7:
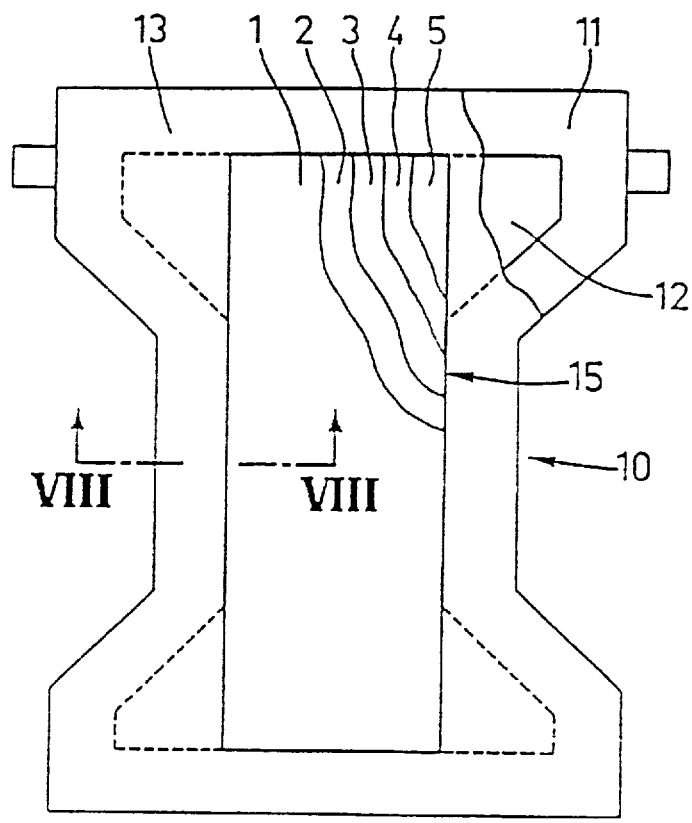
FIG. 7, a top view, with partial cutaway, of an absorbent article of hygiene such as a diaper, comprising a crotch region strip, according to the invention, arranged on the inner surface of the surface web.
Figure 8:
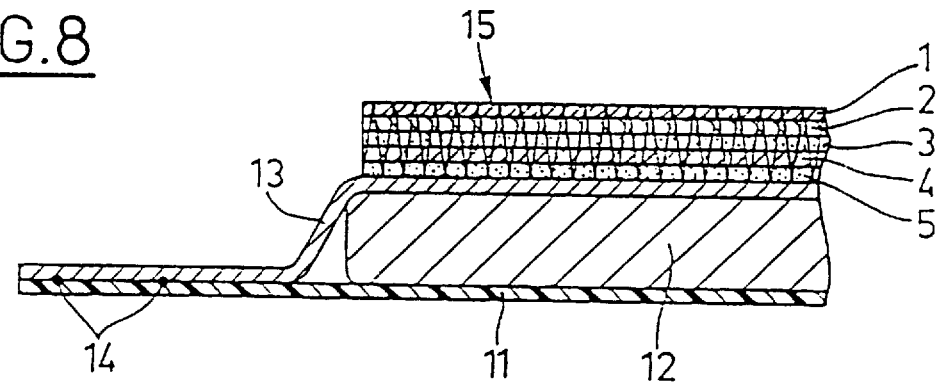
FIG. 8, a view in section along the line VIII—VIII of FIG. 7.

With reference to FIGS. 7 and 8, an absorbent article of hygiene 10, such as a diaper similar to that of FIGS. 5 and 6 has been shown, which comprises an outer layer 11 made of a flexible material which is impermeable to body fluids, on which there is arranged an absorbent mat or pad 12 which is permeable to body fluids and smaller in size than the outer layer 11. On this absorbent pad 11 there is a surface web 13 made up of a conventional nonwoven material, for example made of polypropylene fibers of 2.2 denier, similar in size to that of the outer layer 11 and bonded to the outer layer by any appropriate means, for example adhesive bonding 14. On this surface web 13 is arranged a crotch region strip 15 which is permeable to body fluids, made of nonwoven material according to the invention, such as, for example, the material of FIG. 4. This crotch region strip 15 is generally of rectangular shape which has a width similar to that of the pad 12 in the crotch region and a length similar to that of this pad 12. According to the invention this crotch region strip 15 comprises at least two layers of nonwoven, five layers 1–5 in the embodiment shown, the denier of which decreases from the innermost layer 1 to the outermost layer 5 which is in contact with the surface web 13. This crotch region strip 15 can be bonded to the inner surface of the surface web made of conventional nonwoven 13 by any conventional means such as adhesive bonding, heat-sealing, ultrasonic welding or needling.

As previously, the layer 5 made of fibers of lower denier is the layer of the crotch region strip which is the nearest to the absorbent pad, whereas the layer 1 made of fibers of higher denier is found to be the layer furthest away from the pad 12 and, in this embodiment, the layer intended to come into contact with the user's body. As previously, a rapid drying-out of the upper layer(s) of the crotch region strip is obtained, and an increased barrier effect in respect of rewetting.

Figure 9:
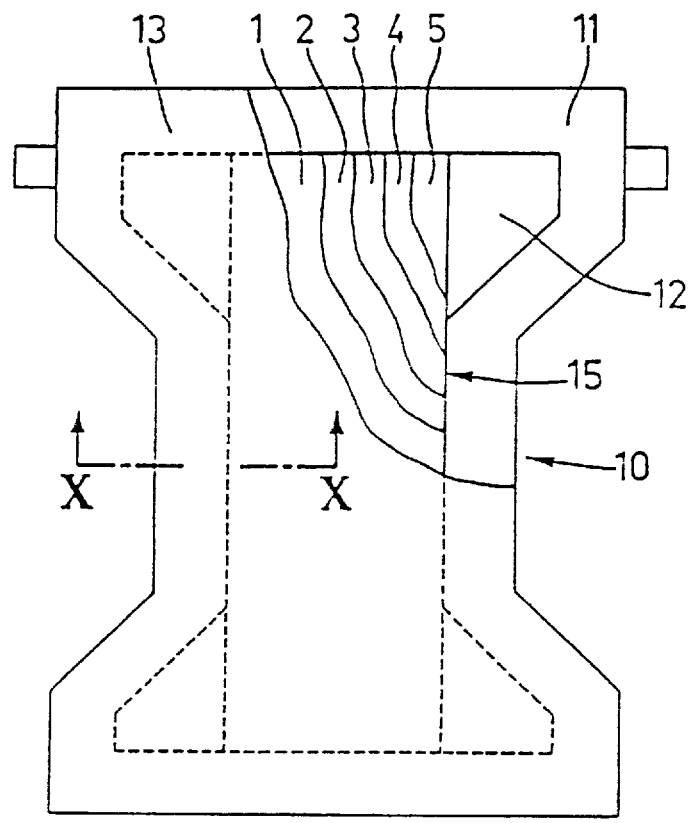
FIG. 9, a top view, with partial cutaway, of an absorbent article of hygiene such as a diaper, comprising a crotch region strip according to the invention, arranged between the surface web and the absorbent pad.
Figure 10:
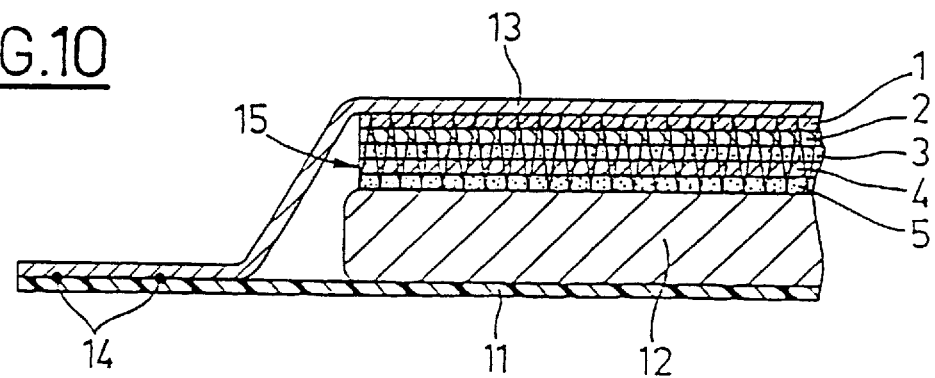
FIG. 10, a view in section along the line X—X of FIG. 9.

With reference to FIGS. 9 and 10, an absorbent article of hygiene 10 similar to that of FIGS. 7 and 8 has been shown, but in which the crotch region strip 15 is arranged between the surface web made of conventional nonwoven material 13 and the absorbent pad 12. In this embodiment, with the exception of the location of the crotch region strip 15, all the other components are identical to those of FIGS. 7 and 8. In this embodiment the crotch region strip 15 is arranged between the surface web 13 and the pad 12 so that the layer 1 made of fibers of higher denier is the innermost layer, that is to say the layer closest to the surface web 13, and the layer 5 made of fibers of lower denier is the outermost layer of the strip, that is to say the layer in direct contact with the inner surface of the absorbent pad 12. The crotch region strip 15 made of multilayer nonwoven material according to the invention may be joined either to the outer surface of the surface web 13 or to the inner surface of the absorbent pad by any appropriate means such as, for example, adhesive bonding, heat-sealing, ultrasonic welding or needling.

The diaper thus produced exhibits a rapid drying out of the inner surfaces in the crotch region and an increased barrier effect in respect of rewetting.

The following examples are given by way of illustration of the present invention.

Comparative Example A

A determination was made of the rate of break-through and the rewetting resistance of a commercial diaper (Peaudouce Action girl® corresponding to the 8–18 kg size, in which the total weight is 59.2 g, the weight of the absorbent pad 48.6 g including 4.8 g of superabsorbent material) and which comprises a conventional surface web made of nonwoven of polypropylene fibers of the spin-bonded type (spun nonwoven) which has a weight per unit area of 20 g/m². The results are given in Table 1 below.

Comparative Example B

A determination was made of the rate of break-through and the rewetting resistance of another commercial diaper of identical size to that of Comparative example A and which has an identical surface web (Peaudouce Action boy®, in which the total weight is 59.4 g, the weight of the absorbent pad is 49 g, including 4.94 g of superabsorbent material). The results are given in Table 1 below.

Comparative Example C

The surface web of the diaper of Comparative example B was replaced with three superposed layers of polyester fibers of 6.6 deniers and a weight per unit area of 41 g/m², that is a total weight per unit area of 123 g/m². The rate of break-through and the rewetting resistance were determined. The results are given in Table 1.

Comparative Example D

The surface web of the diaper of Comparative example B was replaced with six superposed layers of polyester fibers of 3.3 deniers and a weight per unit area of 22 g/m², that is a total weight per unit area of 132 g/m². The rate of break-through and the rewetting resistance were determined. The results are given in Table 1.

Comparative Example E

The surface web of the diaper of Comparative example B was replaced with six layers of polyester fibers of 1.5 deniers and a weight per unit area of 22 g/m², that is a total weight per unit area of 132 g/m². The rate of break-through and the rewetting resistance were measured. The results are given in Table 1.

EXAMPLE 1

A surface web made of a composite material according to the invention, comprising two layers of polyester fibers bonded together by needling, was added to the surface web of the diaper of Comparative example A. The polyester fibers of the inner layer were of 6.6 deniers and this layer had a weight per unit area of 41 g/m². The polyester fibers of the outer layer were of 3.3 deniers and this layer had a weight per unit area of 22 g/m². This outer layer is arranged in contact with the conventional surface web of the diaper.

The rate of break-through and the rewetting resistance were determined. The results are given in Table 1.

Comparative Example 1a

The same structure as in Example 1 was produced, but reversing the position of the layers of the composite material according to the invention in relation to the conventional surface web of the diaper, that is to say by placing the layer of fibers of 6.6 deniers directly on the conventional surface web of the diaper. The rate of break-through and the rewetting resistance were determined. The results are given in Table 1.

EXAMPLE 2

The same structure as in Example 1 was produced, but using polyester fibers of 1.5 deniers for the outer layer made of fibers of lower denier. This outer layer had a weight per unit area of 22 g/m². This outer layer of fibers of 1.5 deniers was arranged directly on the conventional surface web of the diaper. The rate of break-through and the rewetting resistance were determined. The results are given in Table 1.

Comparative Example 2a

The same structure as in Example 2 was produced, but reversing the position of the layers of the composite material according to the invention in relation to the conventional surface web of the diaper, that is to say by placing the layers of fibers of 6.6 deniers directly on the conventional surface web of the diaper. The rate of break-through and the rewetting resistance were determined. The results are given in Table 1.

In addition, comparison of the results obtained between Examples 1 and 2 and Comparative examples 1a and 2a shows the greater the increase in the difference in the decrease between the values of the deniers of the inner layer and of the outer layer which are superposed, the better are simultaneously the rate of break-through and the rewetting resistance. It is noted, moreover, in Comparative examples 1a and 2a that, when the respective position of the two layers is reversed, the rewetting resistances are reduced thereby. Finally, comparison of the results obtained in Comparative examples C, D and E with those of Comparative example B shows that the use, as replacement for a conventional surface web, of a composite web which has a substantially constant weight per unit area, made up of a number of layers of nonwoven material of the same denier, makes it possible to

TABLE 1

|  | Comparative example A | Comparative example B | Comparative example C | Comparative example D | Comparative example E | Example 1 | Comparative example 1a | Example 2 | Comparative example 2a |
|---|---|---|---|---|---|---|---|---|---|
| 1st break-through time (s) | 53 | 85 | 38 | 39 | 38 | 55 | 48 | 36 | 45 |
| 2nd break-through time (s) | 178 | 313 | 40 | 62 | 69 | 83 | 77 | 58 | 55 |
| 3rd break-through time (s) | 211 | 320 | 52 | 65 | 78 | 91 | 87 | 67 | 69 |
| Rewetting resistance (g) | | | | | | | | | |
| after 20 minutes | 4.10 | 0.60 | 0.20 | 0.30 | 0.30 | 0.30 | 0.25 | 0.20 | 0.30 |
| after 40 minutes | 36.50 | 7.20 | 0.80 | 21.70 | 30.50 | 1.30 | 6.70 | 0.70 | 5.10 |
| after 60 minutes | 57.10 | 40.30 | 15.80 | 45.00 | 53.00 | 27.80 | 30.90 | 17.20 | 26.50 |

The break-through times and the rewetting resistance were determined as follows:

The finished products are conditioned at 23° C. and 50% relative humidity for 24 hours before the tests.

A 7×7 cm sheet of Plexiglas® perforated in its center is placed in the center of the surface web of the tested article. 100 cm³ of a saline solution containing 9 g/l of sodium chloride in distilled water were poured into the orifice in the sheet by means of a separating funnel, the flow of the funnel being adjusted to have a constant high level in the orifice in the sheet. The time elapsed between the beginning of the entry of the saline solution and the instant at which the saline solution has disappeared into the article is measured. The measured time constitutes the first break-through time.

Six Dimar ED 939® filter papers cut into squares of 10.2×10.2 cm are then weighed. A 10.2×10.2 cm weight of 3.5 kg is then placed for 10 minutes on the surface web of the tested article, after the perforated sheet has been taken off. Once 10 minutes have elapsed, the six filter papers are placed under the weight and left for another 10 minutes. At the end of this period the weight and the filter papers are removed. The filter papers are weighed. The difference in weight, in grams, between the first and second weighing gives a measure of the rewetting resistance after 20 minutes.

The above procedure is repeated twice with the same article, 24 filters being employed after the second addition of saline solution and 30 filters after the third addition, respectively. The second and third break-through times are thus obtained, together with the rewetting resistance after 40 and 60 minutes.

A comparison of the results obtained between Examples 1 and 2, on the one hand, and the Comparative example A, on the other hand, shows that the use of a composite nonwoven according to the invention in addition to a conventional surface web improves the rate of break-through of the liquid very markedly (more than 50% at the third test) although the total weight per unit area of the surface web is increased by 63 g/m².

improve the rate of break-through, the rewetting resistance is particularly strengthened only when the denier of the composite web is high, and therefore when the gradient between the average porosity of the absorbent pad and of the surface web is greatest, and for a high total weight per unit area.

What is claimed is:

1. An absorbent article of hygiene comprising:
   an outer layer which is impervious to body fluids,
   an absorbent pad which is permeable to body fluids and bonded to the outer layer, and
   a surface web which is permeable to body fluids and bonded to the outer layer,
   wherein the surface web comprises a multilayer nonwoven material having at least two superposed layers of natural or synthetic textile fibers, joined together, in which all of the fibers of each of the layers have a denier which is less than a denier of all of the fibers of the next layer in a given direction, such that the layer having the fibers of lowest denier being situated directly on the upper or internal surface of the absorbent pad and the layer having fibers of highest denier being situated closest to a wearer of the absorbent article.

2. The absorbent article of hygiene as claimed in claim 1, wherein the fibers of the successive layers are of the same kind.

3. The absorbent article of hygiene as claimed in claim 1, wherein the multilayer non-woven material comprises untreated layers and layers treated with a hydrophilic surface or oiling agent.

4. The absorbent article of hygiene as claimed in claim 1, wherein the layers of the multilayer nonwoven material are treated and untreated layers alternately.

5. The absorbent article of hygiene as claimed in claim 1, wherein the fibers of the layers are chosen from cellulose, viscose, polyethylene, polypropylene, polyester and ethylene-propylene copolymer fibers.

6. The absorbent article of hygiene as claimed in claim 1, wherein the multilayer non-woven material comprises two layers.

7. The absorbent article of hygiene as claimed in claim 6, wherein the fibers of the layer of fibers of higher denier have a denier of between 3.3 and 6.6 and the fibers of the layer of fibers of lower denier have a denier of between 1.5 and 3.3.

8. The absorbent article of hygiene as claimed in claim 1, wherein the layers of the multilayer nonwoven material are joined by needling or tangling by jets of water.

9. The absorbent article of hygiene as claimed in claim 1, wherein the fibers of the successive layers are of different kinds.

10. The absorbent article of hygiene as claimed in claim 1, wherein all of the fibers in the layer having the fibers of lower denier have a lower denier than the fibers of other of the superposed layers.

11. The absorbent article of hygiene as claimed in claim 1, wherein the layers are joined together by needling.

12. The absorbent article of hygiene as claimed in claim 1, wherein the fibers in one of the layers have a denier in the range of 3.3 and 6, and the fibers in another of the layers have a denier in the range of 1.5 to 3.3.

* * * * *